(12) United States Patent
Makarovsky et al.

(10) Patent No.: US 10,328,003 B2
(45) Date of Patent: Jun. 25, 2019

(54) SOLUBILIZING AGENTS FOR ACTIVE OR FUNCTIONAL ORGANIC COMPOUNDS

(71) Applicant: ISP INVESTMENTS LLC, Wilmington, DE (US)

(72) Inventors: Ilya Makarovsky, Fair Lawn, NJ (US); Michael A. Tallon, Aberdeen, NJ (US); Hani M. Fares, Somerset, NJ (US); Donald I. Prettypaul, Englewood, NJ (US); Krishnamurthy Nacharaju, Hilliard, OH (US); Anna A. Gripp, Whippany, NJ (US); Osama M. Musa, Bedminster, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/735,755

(22) PCT Filed: Jun. 10, 2016

(86) PCT No.: PCT/US2016/036938
§ 371 (c)(1),
(2) Date: Dec. 12, 2017

(87) PCT Pub. No.: WO2016/201260
PCT Pub. Date: Dec. 15, 2016

(65) Prior Publication Data
US 2018/0168970 A1 Jun. 21, 2018

Related U.S. Application Data

(60) Provisional application No. 62/174,995, filed on Jun. 12, 2015.

(51) Int. Cl.
*A61K 8/37* (2006.01)
*A61K 8/49* (2006.01)
(Continued)

(52) U.S. Cl.
CPC .............. *A61K 8/37* (2013.01); *A61K 8/4966* (2013.01); *A61P 17/16* (2018.01); *A61Q 17/04* (2013.01);
(Continued)

(58) Field of Classification Search
None
See application file for complete search history.

(56) References Cited

U.S. PATENT DOCUMENTS

2013/0190502 A1   7/2013   Mashima et al.
2014/0134120 A1   5/2014   Jouy et al.

FOREIGN PATENT DOCUMENTS

WO   WO2006041506 A2   4/2006

OTHER PUBLICATIONS

International Search Report, PCT/US2016/036938 published on Dec. 15, 2016.

*Primary Examiner* — Aradhana Sasan
(74) *Attorney, Agent, or Firm* — William J. Davis; Shaorong Chen; Nathalie Tietcheu

(57) ABSTRACT

A photo protective topical composition, comprising: (i) at least one functional active; and (ii) at least one solubilizing compound having the structure of Formula I:

Formula 1

(Continued)

wherein R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H; wherein the solubilizing compound is present in an amount effective to solubilize said functional active. Also disclosed is a method for treating skin, lips, nails, hair, ears, eyelashes, eyebrows and/or scalp with an effective amount of composition.

22 Claims, 5 Drawing Sheets

(51) Int. Cl.
*A61P 17/16* (2006.01)
*A61Q 17/04* (2006.01)
*C07C 69/76* (2006.01)

(52) U.S. Cl.
CPC ........ *C07C 69/76* (2013.01); *A61K 2800/262* (2013.01); *A61K 2800/49* (2013.01); *C07C 2601/08* (2017.05); *C07C 2601/14* (2017.05)

SOLUBILIZING AGENTS FOR ACTIVE OR FUNCTIONAL ORGANIC COMPOUNDS

FIELD OF INVENTION

This application relates to a topical composition, and more particularly, to a photo protective composition comprising (i) at least one functional active; and (ii) at least one solubilizing compound, wherein the composition is visibly transparent, free of odor and freeze-thaw stable.

BACKGROUND OF THE INVENTION

The skin's appearance and health is continuously affected by various factors including, for example, humidity, UV light, cosmetics, aging, diseases, stress, cigarette smoking, and eating habits, each of which can result in various skin changes. Additionally, certain changes appear on the skin that is characteristic of aging or exposure to sun, many of which are reflected, in particular, by a change in the skin's structure. The main clinical signs of aging of the skin are, in particular, the appearance of fine lines and deep wrinkles, each of which can increase with age. Wrinkles can be caused by both the chronological aging of the skin, and photo aging of skin due to exposure of the skin to sunlight, UV-radiation, and other forms of actinic radiation.

It is well-known that sunlight radiation ranging from 290 to 400 nm is detrimental to organic materials, including human skin, and particularly radiation with wavelengths between 290 and 320 nm, so-called UV-B region is responsible for the occurrence of erythema and sunburns, whose severity depends on exposure length. Furthermore, it has been ascertained that radiation between 320 and 400 nm, so-called UV-A, which is responsible for skin tanning, can cause alterations and important damages in skin, especially in the case of sensitive skin, or in the case of continuous exposure to the radiation. It has been shown that UV-A radiation, besides causing damage to elastin and collagen, the consequence of which is skin ageing, can also be the cause of a number of phototoxic and photo allergic reactions. Moreover, the harmful action of UV-B can also be enhanced by the presence of UV-A.

Many commercial products, e.g., personal care, sunscreen, pharmaceutical, agricultural and industrial compositions which contain active or functional compounds are available. These active or functional compounds often require solubilization in the form of a solution, emulsion or dispersion, in aqueous or non-aqueous form. For example, sunscreen formulations containing aromatic compounds such as avobenzone (Escalol®517) and/or benzophenone-3 (Escalol®567) active UVA/UVB absorbing ingredients require a solubilization to prevent crystallization. Several such solubilizers are known, e.g., ethyl benzoate and a $C_{12}$-$C_{15}$ alkyl benzoate (Finosolve TN; Witconol APM manufactured and marketed by Witco). However, the former compound is a strong irritant, and the latter is only a poor solvent for avobenzone and benzophenone-3.

U.S. Pat. Nos. 7,166,275 and 7,691,363 assigned to ISP Investments Inc. disclose compositions of an active or functional organic compound solubilized in a phenyl ethyl ester which is an aryl carboxylic ester of 2-phenylethyl alcohol. The phenyl ethyl ester can be 2-phenylethyl benzoate, toluate or phthalate. The active or functional organic compound can be a solid organic compound, e.g., a personal care, cosmetic, sunscreen, pharmaceutical, agricultural or industrial compound. Preferred actives include active sunscreen ingredients, e.g., UVA and/or UVB sunscreens such as avobenzone and/or benzophenone-3. X-Tend™ 226, marketed by Ashland Specialty Ingredients, is the ester of 2-phenylethyl alcohol and benzoic acid. It has a high solubilizing capacity for solid organic sunscreen materials such as oxybenzone and avobenzone and has achieved widespread commercial acceptance. It exhibits excellent skin feel and also increases the critical wavelength and the UVA/UVB ratio of some formulations. It can also be used to enhance shine in hair sprays, shine sprays, or styling creams. It has colorless to light yellow liquid with faint odor of roses.

U.S. Pat. No. 7,785,573 assigned to ISP Investments Inc. discloses active or functional organic compounds solubilized by an ester of an aryl alcohol, e.g., phenethyl, benzyl or substituted benzyl alcohol, and an alkyl or cycloalkyl carboxylic acid, or by a carbonate of the aryl alcohol and an alkyl or cycloalkyl carbonic acid.

U.S. Pat. No. 7,364,721 assigned to L'Oreal, discloses a cosmetic composition including an active or functional organic compound, which is solubilized by a safe and effective organic solvent such as an aryl carboxylic ester of 2-phenylethyl alcohol, e.g. 2-phenylethyl benzoate, 2-phenylethyl toluate or di-2-phenylethyl phthalate.

Despite the solutions proposed by the aforementioned patents and other approaches described in the published literature, there still exists a need for an effective cosmetic or dermatological composition to reduce skin damage by exposure to UV radiation.

Thus it is desired to provide improved cosmetic or dermatological compositions having better solubilizing compounds that are capable of solubilizing functional or organic compounds employed therein, particularly at low temperatures, and at the same time having greater regulatory acceptability and consumer acceptability such as reduced irritation or hypoallergic, odorless (free of pungent odor) and/or colorless that causes inconvenience to users.

Accordingly, the primary objective of the present application is to provide a photo protective composition capable of eliminating or reducing undesired properties such as instability, irritation, allergy, pungent odor, color, and other related issues.

SUMMARY OF THE INVENTION

In one aspect, the present application provides a photo protective, topical composition comprising (i) at least one functional active; and (ii) at least one solubilizing compound, having the formula I:

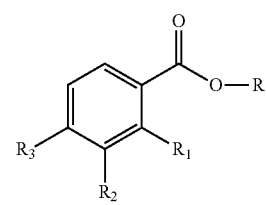

Formula 1 wherein, R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H; wherein said solubilizing compound is present in an amount effective to solubilize said functional active.

In another aspect, the present application provides a solubilizing compound (or agent) selected from the group consisting of cyclohexyl 2-toluate, cyclohexyl 3-toluate, cyclohexyl 4-toluate, cyclohexylmethanol 3-toluate, cyclopentyl 3-toluate, cycloheptyl-3-toluate and combinations thereof present in an amount of about 0.1% wt./wt. to about 70% wt./wt., preferably 0.1% wt./wt. to about 50% wt./wt. of the total photo protective topical composition.

In another aspect, the present application provides a photo protective topical composition formulated into an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous formulation, an anhydrous spray, an anhydrous gel, an anhydrous dry gel, an aqueous gel, a gel cream SPF 20, a SPF 30 cream, an alcoholic solution, a hydro-alcoholic solution, a milk, a lotion, a powder, a stick, a roll-on, a mist, a wipe, a wax, a mousse, an aerosol, a balm, a patch, a pomade, a pump spray, a solution, a towelette, paste, powder or a spray.

In still another aspect, the present application provides a method for cosmetically treating or caring for the skin, lips, nails, hair, ears, eyelashes, eyebrows and/or scalp comprising topically applying thereon, an effective amount of the photo protective topical composition of the present application.

In yet another aspect, the present application provides a method for photo protecting the exposed and/or unexposed skin, nails, hair, lips, ears, eyebrows, eyelashes, and/or scalp, against the damaging effects of ultra violet (UV) irradiation comprising topically applying thereon, an effective amount of the cosmetic/dermatological composition of the present application.

In yet another aspect, the present application provides photo protective topical sunscreen compositions for the UV protection of human skin and/or hair comprising: (a) about 1% wt./wt. to about 70% wt./wt. of at least one active sunscreen agent; (b) about 0.1% wt./wt. to about 50% wt./wt. of at least one solubilizing compound selected from cyclohexyl 3-toluate, cyclohexyl 4-toluate or a combination thereof; and (c) about 1% wt./wt. to about 80% wt./wt. of at least one topically applicable, cosmetically or dermatologically acceptable carrier.

BRIEF DESCRIPTION OF THE FIGURES

Further embodiments of the present invention can be understood with reference to the appended figures.

DETAILED DESCRIPTION OF THE INVENTION

Figure 1:
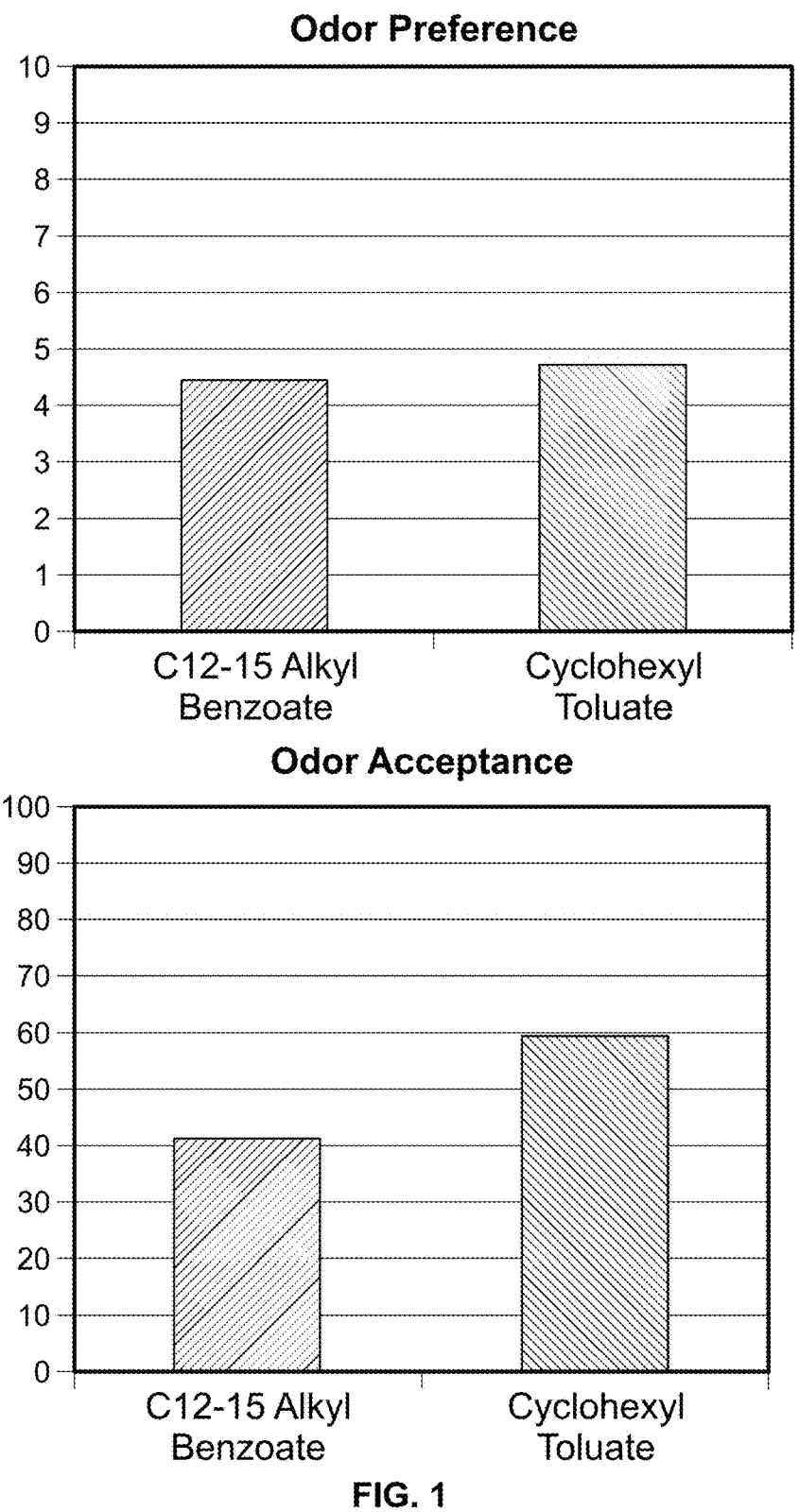
FIG. 1 illustrates consumer odor evaluations for C12-15 alkyl benzoate prior art and inventions.

While this specification concludes with claims particularly pointing out and distinctly claiming that which is regarded as the invention, it is anticipated that the invention can be more readily understood through reading the following detailed description of the invention and study of the included examples.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the disclosure, the following terms, unless otherwise indicated, shall be understood to have the following meanings.

The use of the word "a" or "an" when used in conjunction with the term "comprising" mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

All percentages, ratio, and proportions used herein are based on a weight basis unless other specified.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un recited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAAB-CCCC, CBBAAA, CABABB, and so forth. The skilled artisan will understand that typically there is no limit on the number of items or terms in any combination, unless otherwise apparent from the context.

The terms "preferred," "preferably", and variants thereof, refer to embodiments of the invention that afford certain benefits, under certain circumstances. However, other embodiments are also preferred, under the same or other circumstances. Furthermore, the recitation of one or more preferred embodiments does not imply that other embodiments are not useful and is not intended to exclude other embodiments from the scope of the invention.

References herein to "one embodiment" or "one aspect" or "one version" or "one objective" of the application include one or more such embodiment, aspect, version or objective, unless the context clearly dictates otherwise.

The term "each independently selected from the group consisting of" means when a group appears more than once in a structure, that group can be selected independently each time it appears.

The term "alkyl" refers to a functionalized or unfunctionalized monovalent straight-chain or branched-chain $C_1$-$C_{60}$ group optionally having one or more heteroatoms. Particularly, an alkyl is a $C_1$-$C_{45}$ group and more particularly, a $C_1$-$C_{30}$ group. As used herein, the term alkyl refers to $C_1$-$C_4$ group.

The term "branched" refers to any non-linear molecular structure. The term includes both branched and hyper-branched structures.

The term "cosmetically acceptable ingredient" means any ingredient/compound or mixture of ingredients/compounds or compositions that are typically employed to produce other desirable effects in personal care compositions.

The term "cosmetic/dermatological composition" as used herein is intended to describe compositions for topical application to human skin, including leave-on and wash-off products.

The terms "effective amount" and "effective use level" refer to a sufficient amount of functional active or solubilizing agent employed to provide desired performance attributes, stability, efficacy, product aesthetics, and the like.

The term "hypoallergic" should be construed in a broad sense as compound with reduced irritation and which doesn't sensitize the skin or hair after topical application.

The term "free of odor" should be construed in a broad sense as property of a substance that does not have any characteristic odor or smell.

The term "freeze-thaw stable" as used herein refers to a kind of stability test, wherein the sample under test is subjected to low temperature as low as 0° C. and then thawing the sample to temperatures as high as 95° C. This test describes the ability of the product to remain stable under varied temperature conditions.

The term, "functional active" as used herein refers to, e.g., chemically-active, pharmaceutically-active, or nutraceutically active ions, molecules, complexes or polymers. It includes a personal care, cosmetic, pharmaceutical, and nutraceutical active compounds. Preferably, the functional active is a sunscreen containing UVA and/or UVB active organic or a mineral photo protective agent that is water-soluble or lipo soluble or insoluble in cosmetic solvents commonly employed.

The terms "personal care composition" and "cosmetics" refer to compositions intend for use on or in the human body, such as skin, sun, hair, oral, cosmetic, eyebrows, eyelashes, and preservative compositions, including those to alter the color and appearance of the skin and hair.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

The term "pharmaceutical active" should be construed in a broad sense as including any active ingredient considered to have a therapeutic effect when delivered to a subject in need thereof and further being regulated by drug authorities like CDER, EMEA, TAG, etc. Pharmaceutically active ingredients can act systemically upon oral consumption, or locally such as when present in the buccal cavity, on the skin, etc. They can also be delivered across the skin as in transdermal drug delivery systems.

The term "photo protective composition" includes cosmetic compositions, personal care, pharmaceutical compositions and/or nutraceutical compositions.

The term "photo protective" as used herein refers to the ability of a functional active, preferably sunscreen active, to maintain its integrity when exposed to sunlight when combined with the cycloalkyl toluate based compound. A photo protective composition generally has an SPF (sunscreen protection factor) of at least 6, for example, and preferably at least 30, 45, 60 or 100. The SPF is duly defined in "A new substrate to measure sunscreen protection factors throughout the ultraviolet spectrum", *J. Soc. Cosmet. Chem.,* 40, 127-133, 1989 which is hereby incorporated by reference in its entirety.

The term "photostable" as used herein refers to the ability of a molecule to remain intact with irradiation.

The term "skin" as used herein includes the skin on the face, neck, chest, back, abdomen, arms, hands, legs, feet, and scalp.

The term "SPF" as used herein refers to sun protection factor (SPF)—defined as the dose of UVR required to produce 1 minimal erythema dose (MED) on protected skin after the application of 2 mg/cm² of product divided by the UVR required to produce 1 MED on unprotected skin.

The term "sun care composition" refers to any composition intended for use on the human body for protection from harmful or undesirable radiation from sun rays.

The personal care industry requires improved cosmetic and dermatological compositions, particularly those comprising sunscreen or sun care actives. One of the biggest technological challenges for sunscreen compositions is to effectively and completely solubilize the functional active which often is lipophilic and at the same time provide protection against harmful UV radiations. The present application provides an effective means of meeting the aforementioned unmet need.

What is described herein is a photo protective, topical composition comprising: at least one functional active and at least one cycloalkyl toluate based solubilizing compound, wherein, said solubilizing compound is present in an amount effective to solubilize said functional active. Further, the photo protective topical composition is visibly transparent, free of odor, hypoallergic, and free-thaw stable.

In accordance with the present invention, there is provided a photo protective, topical composition comprising: (i) at least one functional active; and (ii) at least one solubilizing compound having the formula I:

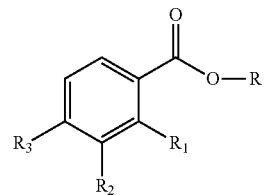

Formula 1 wherein R is a $C_5$-$C_{10}$ cycloalkyl or a linear or branched alkylcycloalkyl, wherein the ring size is $C_5$-$C_7$; $R_1$, $R_2$ and $R_3$ are H or a linear or branched $C_1$-$C_4$ alkyl, provided that at least two of $R_1$, $R_2$ and $R_3$ are H; and wherein said solubilizing compound is present in an amount effective to solubilize said functional active.

Accordingly, "an effective amount" is the amount of at least one solubilizing compound (or agent) required to solubilize at least one functional active. The solubilizing compound of the present application is present in an effective amount of from about 0.1% wt./wt. to 70% wt./wt. of the total composition. Other non-limiting ranges for solubilizing compound include 0.1% to 1%, 1% to 5%, 5% to 10%, 10% to 15%, 15% to 20%, 20% to 25%, 25% to 30%, 30% to 50% or 50% to 70%. However, the preferred range of solubilizing compound employed to solubilize at least one functional active is in the range of from about 5% wt./wt. to 10% wt./wt. of the total composition.

In one preferred embodiment, the present application provides at least one solubilizing compound (or agent) to solubilize the functional actives, and wherein, the solubilizing compound belongs to a group of cycloalkyl toluates. Non-limiting yet preferred solubilizing compounds can be selected from the group consisting of cyclohexyl 2-toluate, cyclohexyl 3-toluate, cyclohexyl 4-toluate, cyclohexylmethanol 3-toluate, cyclopentyl 3-toluate, and cycloheptyl-m-toluate, alone or in combinations thereof. The representative structures of these non-limiting compounds would include:

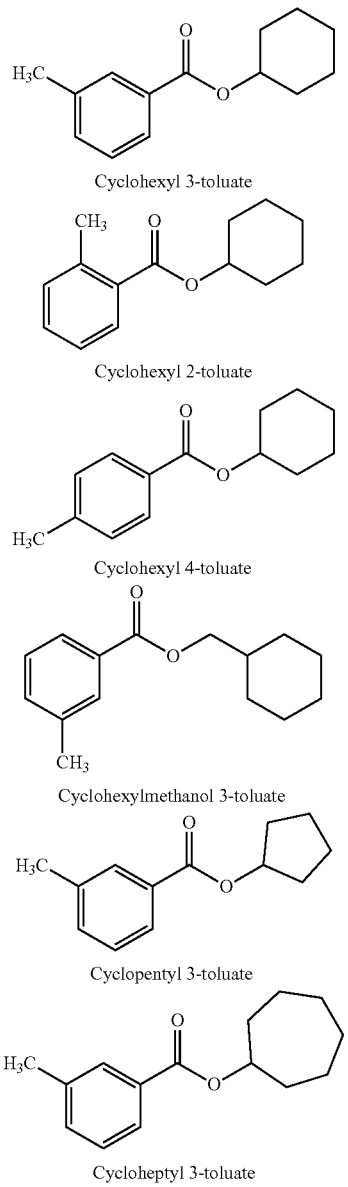

Cyclohexyl 3-toluate

Cyclohexyl 2-toluate

Cyclohexyl 4-toluate

Cyclohexylmethanol 3-toluate

Cyclopentyl 3-toluate

Cycloheptyl 3-toluate

According to another preferred and non-limiting embodiment, the composition of present application includes combinations or mixtures of Cyclohexyl-meta-toluate (Cyclohexyl-3-toluate) and Cyclohexyl-para-toluate (Cyclohexyl-4-toluate) in a ratio of from about 70:30 to about 5:95, preferably from about 10 to about 90. This combination advantageously simplifies the formulation systems as it does not necessitate any heating or homogenization prior to use, and therefore, it is freeze-thaw stable.

In another specific and non-limiting embodiment, the present application provides photo protective, topical composition, wherein said composition is a personal care composition, cosmetic care composition, dermatological care composition, pharmaceutical composition, or nutraceutical care composition. Preferably, the composition is personal care composition.

Non-limiting examples of personal care compositions include: a sun care composition, face care composition, lip care composition, eye care composition, skin care composition, after-sun care composition, body care composition, nail care composition, anti-aging composition, insect repellant, oral care composition, deodorant composition, hair care composition, conditioning composition, color cosmetic composition, color-protection composition, self-tanning composition, and foot care composition. In another non-limiting embodiment, the personal care composition is a sun care composition, and more particularly, the sun care composition is a highly effective photo stable and photo protective composition.

In another non-limiting embodiment, the present application provides a sun care composition formulated, for example into products for application to the lips, hair, face, cheeks, neck, area around the eyes, full hands, and body area. Additionally, self-tanning compositions are products that color skin without requiring full sun exposure, are contemplated within the sun care category.

In yet another specific and non-limiting embodiment, the present application provides a functional active selected from personal care actives, cosmetic actives, nutraceutical actives or pharmaceutical actives.

Accordingly, the functional active used in the present application is present in an amount of about 1% wt./wt. to about 90% wt./wt. of the total composition. Other non-limiting ranges for functional actives include 1% to 5%, 5% to 10%, 10% to 15%, 15% to 20%, 20% to 25% or 25% to 30%, 30% to 40%, 40% to 50%, 50% to 60%, 60% to 70%, 70% to 80% and 80% to 90%.

In one non-limiting embodiment, the preferred functional active is a sunscreen active containing UVA and/or UVB actives, organic or mineral photo protective agents which is water-soluble, lipo-soluble or insoluble in commonly known cosmetic solvents.

Non-limiting examples of UV actives include organic and inorganic materials that scatter, absorb, and/or reflect radiation having a wavelength from about 100 nm to about 400 nm. In one particular and non-limiting aspect, the sun care composition protects UV-A, UV-B, and/or UV-C radiation. UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm. Suitable UV actives (or UV filters) that can be selected for inclusion in the personal care compositions most likely will depend on local regulations. It is well known that commercially available sunscreens generally contain combinations of multiple sunscreen actives.

Non-limiting examples of sunscreens (UV actives) useful in the present application include octyl salicylate; p-aminobenzoic acid, PEG-25PABA, Ethylhexyl dimethyl PABA, pentyl dimethyl PABA, octyl dimethyl PABA, amyl dimethyl PABA, benzophenone-1, benzophenone-2, benzophenone-3, benzophenone-4, benzophenone-5, benzophenone-6, benzophenone-8, benzophenone-9, 2-(2H-benzotriazole-2-yl)-4,6-di-tert-pentylphenol, ethyl-2-cyano-3,3-diphenyl acrylate, homo menthyl salicylate, his-ethyl hexyloxyphenol methoxy phenyl triazine (bemotrizinol), methyl-(1,2,2,6,6-pentamethyl-4-piperidyl)-sebacate, 2-(2H-benzotriazole-2-yl)-4-methylphenol, diethylhexyl butamido triazone, 4,6-bis-(octylthiomethyl)-o-cresol, Poly(4-hydroxy-2,2,6,6-tetramethyl-1-piperidine ethanol-alt-1,4-butanedioic acid), red petroleum, octocrylene, isoamyl-p-methoxycinnamate, drometrizole, drometrizole trisiloxane, bisoctrizole, 2,4-di-tert-butyl-6-(5-chloro-2H-benzotriazole-2-yl)-phenol, 2-hydroxy-4-octyloxy benzophenone, diisopropyl methylcinnamate, 2-(1,1-dimethylethyl)-6-[[3-(1,1-demethylethyl)-2-hydroxy-5-methylphenyl]methyl-4-methylphenyl-acrylate, menthyl anthranilate, butyl methoxy dibenzoyl methane, 2-ethoxyethyl p-methoxycinnamate, benzylidene camphor sulfonic acid, dimethoxyphenyl-[1-(3,4)]-4,4-dimethyl1,3-pentanedione, N,N'-hexane-1,6-diylbis-[3-(3,5-di-tert-butyl-4-hydroxyphenyl-propionamide)], pentaerythritol tetrakis [3-(3,5-di-tert-butyl-4-hydroxyphenyl) propionate], 2,6-di-tert-butyl-4-[4,6-bis(octylthio)-1,3,5-triazin-2-ylamino] phenol, 2-(2H-benzotriazole-2-yl)-4,6-bis(1-methyl-1-phenylethyl)phenol, trolamine salicylate, diethylanolamine p-methoxycinnamate, polysilicone-15, 4-methylbenzylidene camphor, n-phenyl-benzenamine, reaction products with 2,4,4-trimethylpentene, (2-ethylhexyl)-2-cyano-3,3-diphenylacrylate, digalloyl trioleate, polyacrylamido methylbenzylidene camphor, glyceryl ethylhexanoate dimethoxycinnamate, 1,3-bis-[(2'-cyano-3',3'-diphenylacryloyl)oxy]-2,2-bis-{[(2'-cyano-bis-(2,2,6,6-tetramethyl-4-piperidyl)-sebacate, 1,3,5-tris(3,5-di-tert-butyl-4-hydroxybenzyl)-1,3,5-triazine-2,4,6(1H,3H, 5H)-trione, hexamethylendiamine, ethyl-4-bis(hydroxypropyl) aminobenzoate, 6-tert-butyl-2-(5-chloro-2H-benzotriazole-2-yl)-4-methyl phenol, 3,3',3",5,5',5"-hexa-tert-butyl-α-α'-α"-(mesitylene-2,4,6-triyl) tri-p-cresol, ethylhexyl dimethoxybenzylidene dioxoimidazoline propionate, N,N'-bisformyl-N,N'-bis-(2,2,6,6-tetramethyl-4-piperidinyl), 3-benzylidene camphor, terephthalylidene dicamphor sulfonic acid, camphor benzalkonium methosulfate, bisdisulizole disodium, etocrylene, ferulic acid, 2-(2H-benzotriazole-2-yl)-4-(1,1,3,3-tetramethylbutyl)-phenol, 4,6-bis(dodecylthiomethyl)-o-cresol, β-2-glucopyranoxy propyl hydroxy benzophenone, phenylbenzimidazole sulfonic acid, diethylamine hydroxy benzoyl hexylbenzoate, 3',3'-diphenylacryloyl)oxy]methyl}-propane, ethylhexyl p-methoxycinnamate, avobenzone, camphor benzalkonium methosulfate, phenylbenzimidazole sulfonic acid, terephthalidene dicamphor sulfonic acid, benzylidene camphor sulfonic acid, polyacrylamidomethyl benzylidene camphor, ethylhexyl methoxycinnamate, ethylhexyl triazone, diethylhexyl butamido triazone, 4-methyl-benzylidene camphor, 3-benzylidene camphor, methylene-bis-benztriazolyl tetramethylbutylphenol, disodium phenyl dibenzimidazole tetrasulfonate, bisethylhexyloxyphenol methoxyphenol triazine, polysilicone-15, 2,4,6-tris(Diisobutyl 4-aminobenzalmalonate)-s-triazine, inorganic sunscreen selected from titanium dioxide and zinc oxide; micronized or unmicronized mixtures thereof. As noted is contemplated that these actives can be used in combinations.

Sunscreen actives (UV filters) used in present application may include one or more of: Bemotrizinol (Escalol™ S UV filter (Ashland)), Padimate O (Escalol™ 507 UV filter (Ashland)), Avobenzone (Escalol™ 517 UV filter (Ashland)), Octinoxate (Escalol™ 557 UV filter (Ashland)), Oxybenzone (Escalol™ 567 UV filter (Ashland)), Sulisobenzone (Escalol™ 577 UV filter (Ashland)), Octisalate (Escalol™ 587 UV filter (Ashland)), Homosalate (Escalol™ HMS UV filter (Ashland)), and Octocrylene (Escalol™ 597 UV filter (Ashland)).

According to one particularly preferred and non-limiting embodiment, the sunscreen active or agent is bis-ethylhexyloxyphenol methoxyphenol triazine, marketed as Escalol®S by Ashland Specialty Ingredients. The sunscreen composition may additionally comprise at least one additional UV filter and/or a mineral photo protective agent comprising treated or untreated metal oxide pigments or nanopigments as part of the desired composition. Applicants have found that the solubilizers described herein find particular utility at solubilizing bis-ethylhexyloxyphenol methoxyphenol triazine which is known to be difficult to solubilize.

In another preferred embodiment, the present application discloses a photo protective topical personal care composition, wherein the composition is visibly transparent, free of odor and freeze thaw stable.

According to one specific embodiment of the present application, the composition is "visibly transparent" in that the composition is able to be applied to a substrate and light is able to pass through the composition with little or no distortion so that the substrate can be clearly seen through the composition using the eye. Transparency is measured using methods known to those skilled in the art. In this specification, measurements of total absorbance are used to demonstrate the level of transparency achieved using various embodiments of the compositions being claimed.

According to another specific embodiment of the present application, the present composition is "free of odor" in that the sunscreen compositions comprising cyclohexyl toluate and bemotrizinol when subjected to comparison studies with a panel of odor evaluation experts were found to be acceptable. It has been found that Cyclohexyl toluate has appreciable odor preference and odor acceptance ratings over commercial solubilizer C12-15 alkyl benzoate. Even after aging, low odor was observed.

In another specific embodiment, the present application further comprises at least one adjuvant or additive or additional ingredient selected from the group consisting of secondary polymers for improving water-resistance, oils, waxes, solvents, emulsifiers, preservatives, antioxidants, vitamins, perfumes, insect repellants, dyes, pigments, fillers, film formers, buffers, spreading agents, pearlizing agents, electrolytes, acids, bases, fatty substances, organic solvents, ionic or nonionic, hydrophilic or lipophilic thickeners, softeners, humectants, opacifiers, emollients, fragrances, anionic surfactants, cationic surfactants, nonionic surfactants, zwitterionic surfactants, amphoteric surfactants, active agents, polymers, propellants, antioxidants, agents for combating free radicals, alpha-hydroxy acids, moisturizing agents, anti-inflammatory, colorants, pharmaceutically or dermatologically or cosmetically acceptable excipients, skin care or hair care agents, hair styling agents, hair fixative agents, structurants, gelling agents, viscosity modifiers, electrolytes, pH adjusting agents, organo silicones compounds, anti-dandruff agents, antifoaming agents, anti-frizz agents, penetrants, conditioning agents, chelating agents, antimicrobial agents, UV absorbers, natural extracts, carriers, diluents, solvents, pharmaceutical actives, lubricants, combing aids, plasticizers, solubilizers, neutralizing agents, vapor pressure suppressants, bleaching agents, hydrating agents, cosmetic adjuvants and/or additives, protectants, and mixtures thereof.

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), proanthocyanodic oligomers, flavonoids, tetra amino piperidine, erythorbic acid, spermine, cysteine, glutathione, superoxide dismutase, lactoferrin and blends thereof.

Non-limiting examples of inorganic photo protective agents are selected from pigments, preferably nanopigments (mean size of the primary particles: generally from 5 nm to 10 nm, preferably from 1 nm to 5 nm) of treated or untreated metal oxides selected from titanium oxide (amorphous or crystallized in rutile and/or anatase form), iron oxide, zinc oxide, zirconium oxide or cerium oxide.

The additional photo protective agents are generally present in the compositions according to the application in proportions ranging from 0.01% wt./wt. to 70% wt./wt. of the total composition. Other non-limiting ranges for additional photo protective agents include 0.01% to 1%, 1% to 5%, 5% to 10%, 10% to 15%, 15% to 20%, 20% to 25% or 25% to 30%, 30% to 40%, 40% to 50%, 50% to 60%, 60% to 70% by weight of the total composition, and preferably ranging from 0.01% wt./wt. to 10% wt./wt. of the total composition.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof. Preferred preservative include methyl paraben, ethyl paraben, propyl paraben, phenoxy ethanol, benzoic acid and dehydro acetic acid. Non-limiting ranges of preservatives include 0.1% wt./wt. to 10% wt./wt. by weight of the total composition. Other non-limiting ranges include 0.1% to 2%, 2% to 4%, 4% to 6%, 6% to 8% or 8% to 10% by weight of the total composition.

The physiological and cosmetically acceptable medium may consist exclusively of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. Preferred carrier or medium is denatured alcohol, water, propylene glycol, ethanol, trimethylamine, and glycerin. The carrier is present in amount of about 2% wt./wt. to about 90% wt./wt. of the total topical composition. Other non-limiting ranges for carrier include 5% to 10%, 10% to 15%, 15% to 20%, 20% to 25% or 25% to 30%, 30% to 40%, 40% to 50%, 50% to 60%, 60% to 70%, 70% to 80% and 80% to 90% by weight of the total composition.

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof. Non-limiting ranges of vitamins include 0.1% to 10% by weight of the total composition. Other non-limiting ranges include 0.1% to 2%, 2% to 4%, 4% to 6%, 6% to 8% or 8% to 10% by weight of the total composition.

Non-limiting examples of surfactants include anionic surfactant, cationic surfactant, non-ionic surfactant, amphoteric surfactant, or zwitterionic surfactant. Non-limiting ranges of surfactants include 0.1% wt./wt. to 10% wt./wt. of the total composition. Other non-limiting ranges include 0.1% to 2%, 2% to 4%, 4% to 6%, 6% to 8% or 8% to 10% by weight of the total composition.

Non-limiting examples of anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms selected from sarcosinates, taurates, isethionates, sodium lauryl sulfoacetate, sodium laureth carboxylate, and sodium dodecyl benzenesulfonate, sodium and potassium salts of lauroyl sarcosinate, myristoyl sarcosinate, palmitoyl sarcosinate, stearoyl sarcosinate, and oleoyl sarcosinate. Preferred anionic surfactants are selected from sodium lauryl sulfate (SLS) and sodium coconut monoglyceride sulfonates.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutyl phenoxyethyl-dimethylbenzyl ammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants act as germicides in the compositions disclosed herein.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Non-limiting examples of surfactants available commercially include: (1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™ Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol. (2) Avaniel, Cremaphore®, Jordapan®, and Pluracare® from BASF Corp. (3) Miracare® SLB, Mackam® Bab, Mackanate® Ultra SI, Miranol® Ultra, and Miracare® Plaisant from Rhodia. (4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is incorporated hereby in its entirety by reference.

Non-limiting examples of skin conditioning agents include isodecyl neopentanoate, Dicaprylyl carbonate, 2-ethylhexyl isononanoate, Coco-caprylate Caprate, and Isodecyl Salicylate. Non-limiting ranges of skin conditioning agents include 0.1% wt./wt. to 10% wt./wt. of the total composition. Other non-limiting ranges include 0.1% to 2%, 2% to 4%, 4% to 6%, 6% to 8% or 8% to 10% by weight of the total composition.

Non-limiting examples of lubricants useful for the present application is selected from cyclopentasiloxane, diisopropyl adipate, isocetyl alcohol. Non-limiting ranges of lubricants include 0.1% wt./wt. to 10% wt./wt. of the total composition. Other non-limiting ranges include 0.1% to 2%, 2% to 4%, 4% to 6%, 6% to 8% or 8% to 10% by weight of the total composition.

Non-limiting examples of emollient include lauryl lactate, C12-15 Alkyl lactate, methyl glucose sesquistearate and PEG-20 methyl glucose sesquistearate. Non-limiting ranges of emollients include 0.1% wt./wt. to 10% wt./wt. by weight of the total composition. Other non-limiting ranges include 0.1% to 2%, 2% to 4%, 4% to 6%, 6% to 8% or 8% to 10% by weight of the total composition.

Non-limiting examples of suitable silicones include polyalkyl siloxanes, polyaryl siloxanes, polyalkyl aryl siloxanes, silicone gums and resins, polyorgano siloxanes modified by organ functional groups, and blends thereof. Preferred silicones include methicone, caprylyl methicone, and cetyl dimethicone. Non-limiting ranges of silicones include 0.1% wt./wt. to 10% wt./wt. of the total composition. Other non-limiting ranges include 0.1% to 2%, 2% to 4%, 4% to 6%, 6% to 8% or 8% to 10% by weight of the total composition.

Non-limiting examples of emulsifiers include ethoxylated fatty acids, ethoxylated glyceryl esters, ethoxylated oils, ethoxylated sorbitan esters, fatty esters, PEG esters and polyglycerol ester. Preferred emulsifier is glyceryl stearate (and) laureth-23 (1%). Non-limiting ranges of emulsifiers include 0.1% wt./wt. to 10% wt./wt. of the total composition. Other non-limiting ranges include 0.1% to 2%, 2% to 4%, 4% to 6%, 6% to 8% or 8% to 10% by weight of the total composition.

Non-limiting examples of buffering agents used in the present application include alkali or alkali earth carbonates, phosphates, bicarbonates, citrates, borates, acetates, acid anhydrides, succinates and the like, such as sodium phosphate, citrate, borate, acetate, bicarbonate, and carbonate. Non-limiting ranges of buffering agents include 0.1% wt./wt. to 10% wt./wt. by weight of the total composition. Other non-limiting ranges include 0.1% to 2%, 2% to 4%, 4% to 6%, 6% to 8% or 8% to 10% by weight of the total composition.

Non-limiting examples of other additives used in the present application include Ceteareth-20, Hydrogenated Polydecene (and) Trideceth-6, cetyl alcohol, Caprylyl methicone for bringing about desired feel and smoothness to the product.

Non-limiting examples of tanning or browning agents used in the present application include dihydroxy acetone, satin, alloxan, ninhydrin, glyceraldehyde, mesotartaric aldehyde, glutaraldehyde, erythrulose, pyrazoline-4,5-dione derivatives, 4,4-dihydroxy pyrazoline-5 and derivatives thereof. Non-limiting ranges of tanning or browning agents include 0.1% wt./wt. to 10% wt./wt. by weight of the total composition. Other non-limiting ranges include 0.1% to 2%, 2% to 4%, 4% to 6%, 6% to 8% or 8% to 10% by weight of the total composition.

In another specific embodiment, the present application provides a photo protective topical composition formulated into an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous formulation, an anhydrous spray, an anhydrous gel, an anhydrous dry gel, an aqueous gel, a gel cream SPF 20, a SPF 30 cream, an alcoholic solution, a hydro-alcoholic solution, a milk, a lotion, a powder, a stick, a roll-on, a mist, a wipe, wax, a mousse, an aerosol, a balm, a patch, a pomade, a pump spray, a solution, a towelette, paste, powder or a spray.

Non-limiting examples of skin care formulation in the present application include: solutions, oils, lotions, creams, ointments, liquids, gels, solids, W/O emulsions, O/W emulsions, milks, suspensions, micro emulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products. The compositions of the application include skin-washing compositions, particularly in the form of solutions or gels for the bath or shower, or make-up removal products.

The six product categories provided below are included under subset of skin care.

Eye Care—Non-limiting eye care product forms include: mascaras, eye liners, eye shadows, curlers of eye lashes, eyebrow pencils, and eye pencils.

Lip Care—Non-limiting lip care product forms include: lipsticks, lip balms, lip pencils, lip glosses, lip sprays, transparent lip bases, tinted lip moisturizers, and multifunctional color sticks that can also be used for cheeks and eyes.

Nail Care—Non-limiting nail care product forms include: nail polishes, nail varnishes, enamels, nail varnish removers, home-manicure products such as cuticle softeners and nail strengtheners, and artificial nails.

Face Care—Non-limiting face care product forms include: creams, lotions, solutions, oils, liquids, peels, scrubs, emulsions, suspensions, micro emulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

Body Care—Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

Foot Care—Non-limiting foot care product forms include: mousses, creams, lotions, powders, liquids, sprays, aerosols, gels, flakes, and scrubs.

The present photo protective composition is capable of protecting human skin against the harmful effects of irradiation of sun.

It is also contemplated that the personal care compositions are used in products for male and/or female personal grooming and/or toiletry selected from sanitary napkins, baby diapers, adult diapers, feminine products, products for incontinence, and other related products.

In yet another specific embodiment, the present application provides a photo protective topical sunscreen composition for the UV-photo protection of human skin and/or hair comprising: (a) about 1% wt./wt. to about 70% wt./wt. of at least one active sunscreen agent; (b) about 0.1% wt./wt. to about 50% wt./wt. of at least one solubilizing compound selected from cyclohexyl 3-toluate, cyclohexyl 4-toluate or combination thereof; and (c) about 1% wt./wt. to about 80% wt./wt. of at least one topically applicable, cosmetically or dermatologically acceptable carrier.

The present sunscreen composition may further comprise polymers for enhanced performance and feel for the sunscreen compositions selected from α-olefin/Poly vinyl pyrrolidone (Ganex line from Ashland Specialty Ingredients) and Vinyl Acetate: Mono-n-butyl Maleate: Isobornyl acrylate (Advantage-Plus line from Ashland Specialty Ingredients). Addition of these polymers shows increased critical wavelength and UVA/UVB absorbance ratio.

In yet another specific embodiment, the present application provides a method for cosmetically treating or caring for the skin, lips, nails, hair, ears, eyelashes, eyebrows and/or scalp comprising topically applying thereon, an effective amount of the photo protective topical composition comprising (i) at least one functional active; and (ii) at least one solubilizing compound having the formula I:

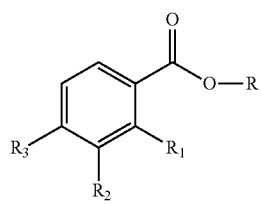

Formula 1 wherein R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H; wherein said solubilizing compound is present in an amount effective to solubilize said functional active.

In yet another specific embodiment, the present application provides a method for photo protecting the exposed and/or unexposed skin, nails, hair, lips, ears, eyebrows, eyelashes, and/or scalp, against the damaging effects of UV-irradiation comprising topically applying thereon, an effective amount of the cosmetic/dermatological composition comprising: (i) at least one functional active; and (ii) at least one solubilizing compound having the formula I

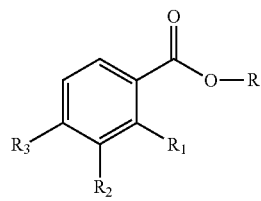

Formula 1 wherein R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H; wherein said solubilizing compound is present in an amount effective to solubilize said functional active.

In order to further illustrate the present application and the advantages thereof, the following specific examples are given, it being understood that same are intended only as illustrative and by no means limitative. In said examples to follow, all parts and percentages are given by weight, unless otherwise indicated.

Example 1: Synthesis of Cyclohexyl 3-Toluate

Cyclohexyl 3-Toluate was prepared by reacting Cyclohexyl alcohol and 3-Toluic acid in the presence of a catalyst, e.g., a Lewis acid and/or organic/inorganic catalyst.

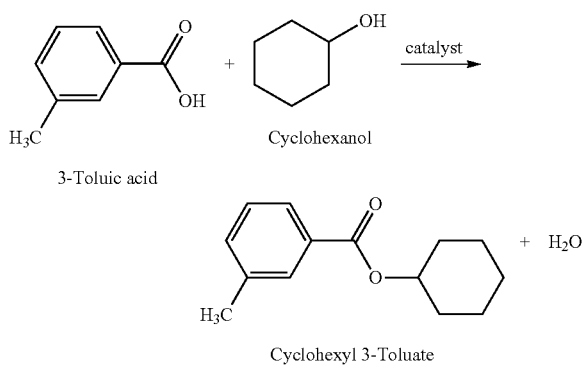

A dry 2-L, 4-neck round bottom flask, fitted with a mechanical stirrer, heating mantle/temperature controller/thermocouple, Dean-Stark trap with reflux condenser and charging port was charged with 601.0 g (6.0 mol) of warm cyclohexanol at 50-80° C. and mixed with 3.3 g of Lewis acid catalyst. The content of the flask was heated to 80-110° C. and 680.8 g (5.0 mol) of 3-Toluic acid was added to the flask with a stirring. The reaction mixture was heated to 230-232° C. and the reaction water was removed. The final reaction mixture with acid number ≤1 mg KOH/g was distilled under vacuum. Yield of Cyclohexyl 3-Toluate: 93%. Purity: 99.6%. Solubility of Escalol S at 25° C.: 35% & Solubility of Avobenzone at 25° C.: 26%

Example 2: Synthesis of Cyclohexyl 4-Toluate

Cyclohexyl 4-Toluate was prepared by reacting Cyclohexyl alcohol and 4-Toluic acid in the presence of a catalyst, e.g., a Lewis acid and/or organic/inorganic catalyst.

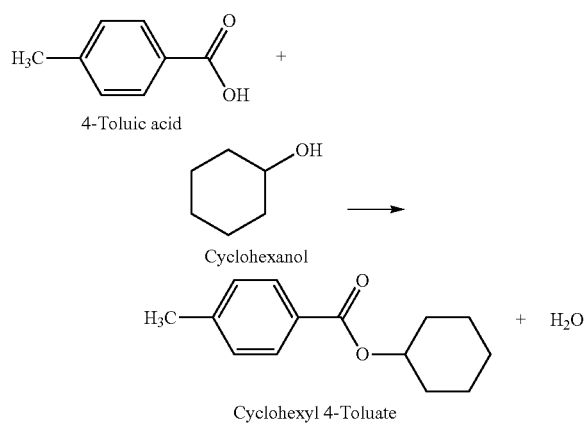

The reaction was run as described above. The flask was charged with 601.0 g (6.0 mol) of warm Cyclohexanol, 3.3 g of Lewis acid catalyst and 680.8 g (5.0 mol) of 4-Toluic acid. The reaction mixture was heated to 230-232° C. and the reaction water was removed. The final reaction mixture with acid number 1.1 mg KOH/g was distilled under vacuum. Yield of Cyclohexyl 4-Toluate: 90%. Purity: 99.7%. Solubility of Escalol S at 25° C.: 36% & Solubility of Avobenzone at 25° C.: 26%

Example 3: Synthesis of Cyclohexyl 2-Toluate

Cyclohexyl 2-Toluate was prepared by reacting Cyclohexyl alcohol and 2-Toluic acid in the presence of a catalyst, e.g., a Lewis acid and/or organic/inorganic catalyst. A dry 1-L, 4-neck round bottom flask, fitted with a mechanical stirrer, heating mantle/temperature controller/thermocouple, Dean-Stark trap with reflux condenser and charging port was charged with 300.5 g (3.0 mol) of Cyclohexanol, 1.6 g of Lewis acid catalyst and 340.4 g (2.5 mol) of 2-Toluic acid. The reaction mixture was heated to 230-232° C. and the reaction water was removed. The final reaction mixture with acid number 3.6 mg KOH/g was distilled under vacuum. Yield of Cyclohexyl 2-Toluate: 94%. Purity 99.4%; Solubility of Escalol S at 25° C.: 37%; Solubility of Avobenzone at 25° C.: 23%

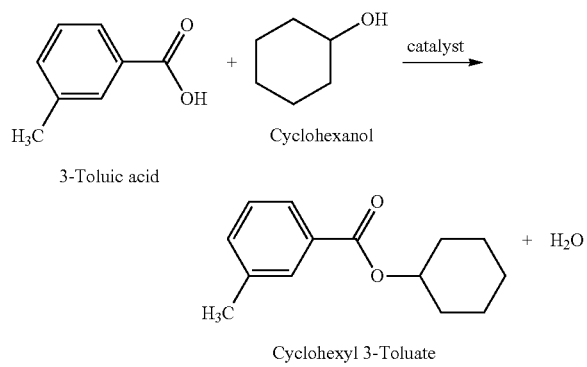

Example 4: Synthesis of Cyclohexyl Toluate (Mixture of Cyclohexyl 3-Toluate and Cyclohexyl 4-Toluate)

Cyclohexyl Toluate mixture was prepared by reacting Cyclohexyl alcohol and the mixture of 3-Toluic acid and 4-Toluic acid in the presence of a catalyst, e.g., a Lewis acid and/or organic/inorganic catalyst.

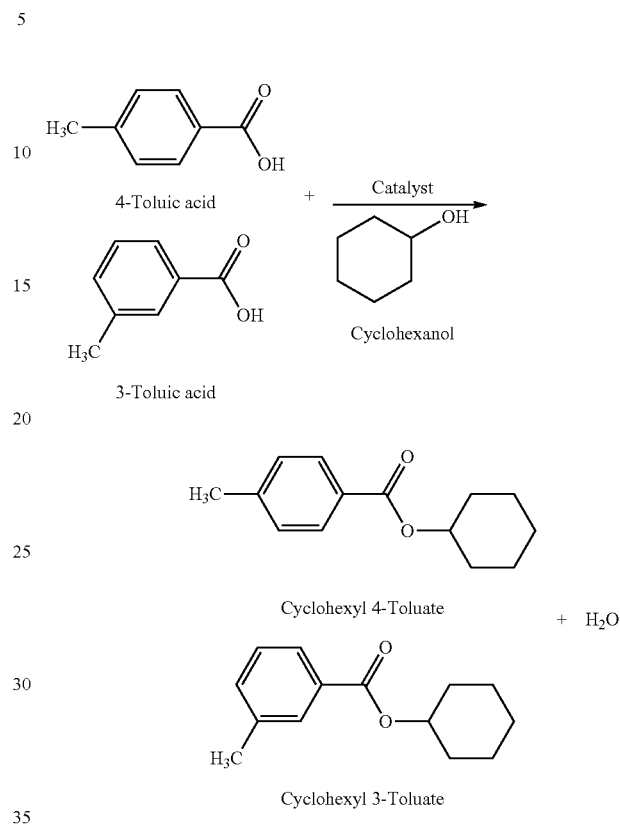

The reaction was run as described above. The flask was charged with 601.0 g (6.0 mol) of warm cyclohexanol, 3.3 g of Lewis acid catalyst and 680.8 g (5.0 mol) of the mixture of 3-Toluic acid with 4-Toluic acid. The reaction mixture was heated to 230-232° C. and the reaction water was removed. The final reaction mixture with acid number <1 mg KOH/g was distilled under vacuum. Yield of Cyclohexyl Toluate: 94%. Purity: 99.8%. Solubility of Escalol S at 25° C.: 36% & Solubility of Avobenzone at 25° C.: 25%

Example 5: Synthesis of Cyclohexylmethanol 3-Toluate

Cyclohexylmethanol 3-Toluate was prepared by reacting Cyclohexylmethanol with 3-Toluic acid in the presence of a catalyst, e.g., a Lewis acid and/or organic/inorganic catalyst.

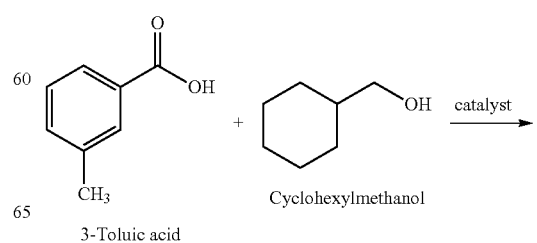

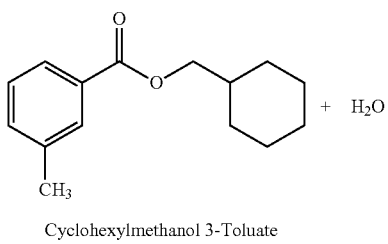

Cyclohexylmethanol 3-Toluate

The reaction was run as described above. The flask was charged with 452.2 g (3.96 mol) of cyclohexylmethanol, 2.3 g of Lewis acid catalyst and 449.3 g (3.3 mol) of 3-Toluic acid. The reaction mixture was heated to 230° C. and the reaction water was removed. The final reaction mixture with acid number <1 mg KOH/g was distilled under vacuum. Yield of cyclohexylmethanol 3-Toluate: 93.4%. Purity: 99.6%. Solubility of Escalol S at 25° C.: 30% & Solubility of Avobenzone at 25° C.: 25%

Example 6: Synthesis of Cyclopentyl 3-Toluate

Cyclopentyl 3-Toluate solubilizer was prepared by reacting Cyclopentyl alcohol with 3-Toluic acid in the presence of a catalyst, e.g., a Lewis acid and/or organic/inorganic catalyst.

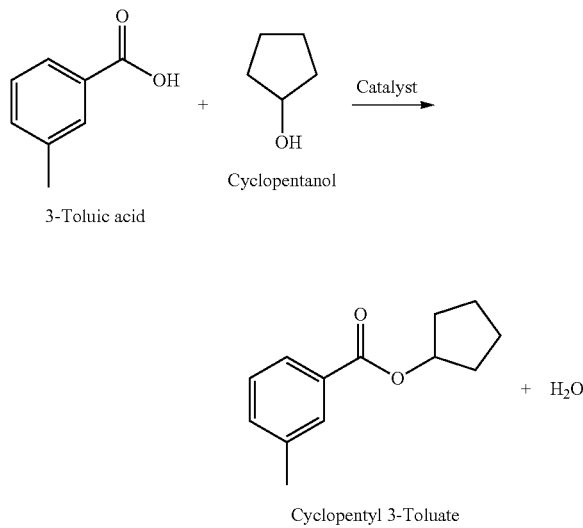

The reaction was run as described above. The flask was charged with 375.0 g (4.4 mol) of Cyclopentyl alcohol, 2.5 g of Lewis acid catalyst and 544.6 g (4.0 mol) of 3-Toluic acid. The reaction mixture was heated to 220° C. and the reaction water was removed. The final reaction mixture with acid number 4.5 mg KOH/g was distilled under vacuum. Yield of Cyclopentyl 3-Toluate: 92%. Purity 99.5%; Solubility of Escalol S at 25° C.: 34%; Solubility of Avobenzone at 25° C.: 28%

Physical properties of the synthesized cycloalkyl aryl esters are disclosed in Table 1, where the physical properties include acid number, American Public Health Association [APHA] color, refractive index and specific gravity.

TABLE 1

Properties of the synthesized cycloalkyl aryl esters

| Compound | Acid number | APHA color | Refractive Index | Specific Gravity |
|---|---|---|---|---|
| Cyclohexyl 3-Toluate | 0.1 | 5.3 | 1.5187 | 1.0381 |
| Cyclohexyl 4-Toluate | 0.1 | 8.0 | 1.5199 | 1.0352 |
| Cyclohexyl 2-Toluate | 1.4 | 15.7 | 1.5214 | 1.0459 |
| Cyclohexyl Toluate (mixture of isomers) | 0.1 | 2.6 | 1.5198 | 1.0361 |
| Cyclohexylmethanol 3-Toluate | 0.1 | <1 | 1.5168 | 1.0276 |
| Cyclopentyl 3-Toluate | 3.5 | 8.9 | 1.5195 | 1.0493 |

Example 7: Solubility of Various Sunscreens in Different Solubilizing Media

TABLE 2

Solubility of sunscreen actives

| | Solubility @ 25° C. | | |
|---|---|---|---|
| Compound | Escalol S | Avobenzone | Oxybenzone |
| Cyclohexyl 2-Toluate | 37 | 23 | 32 |
| Cyclohexyl 3-Toluate | 35 | 26 | 33 |
| Cyclohexyl 4-Toluate | 36 | 26 | 32 |
| Cyclohexyl Toluate (mixture of Cyclohexyl 3-Toluate and Cyclohexyl 4-Toluate) | 36 | 25 | 32 |
| Cyclohexylmethanol 3-Toluate | 30 | 25 | 33 |
| Cyclopentyl m-Toluate | 34 | 28 | 39 |
| Phenethyl benzoate | 22 | 20 | 34 |
| C12-15 alkyl benzoate | 13 | 12 | 15 |

The sunscreens show increased solubility where cyclohexyl compounds were used as demonstrated in Table 2. Escalol®S showed more than a 1.5-fold increase in solubility in the compounds of this application compared with X-Tend 226, which is a solubilizer for sunscreen actives in widespread commercial use.

Figure 2:
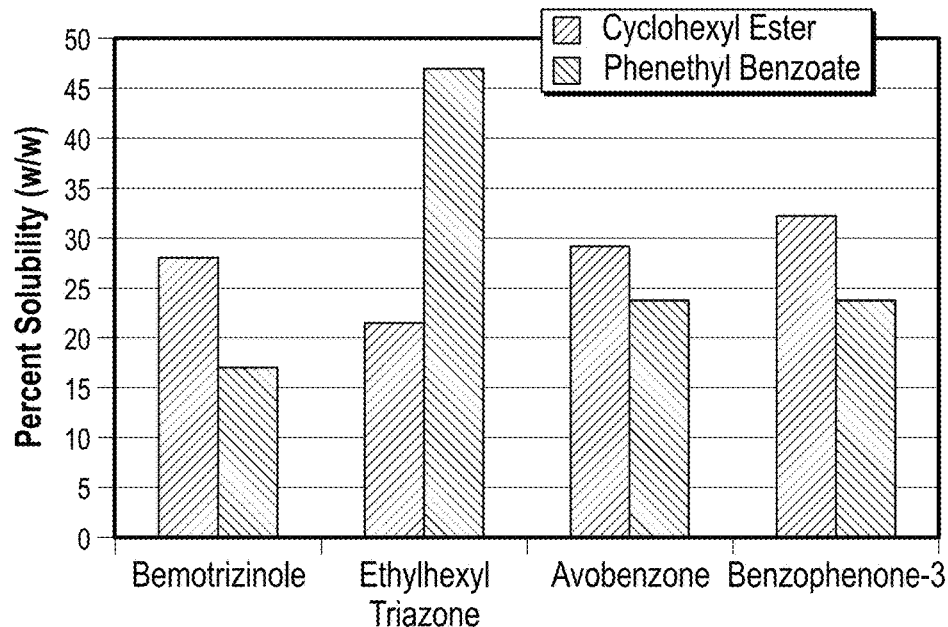
FIG. 2 illustrates solubility of sunscreens in cyclohexyl toluate of the invention and phenethyl benzoate at 25° C.
Figure 3:
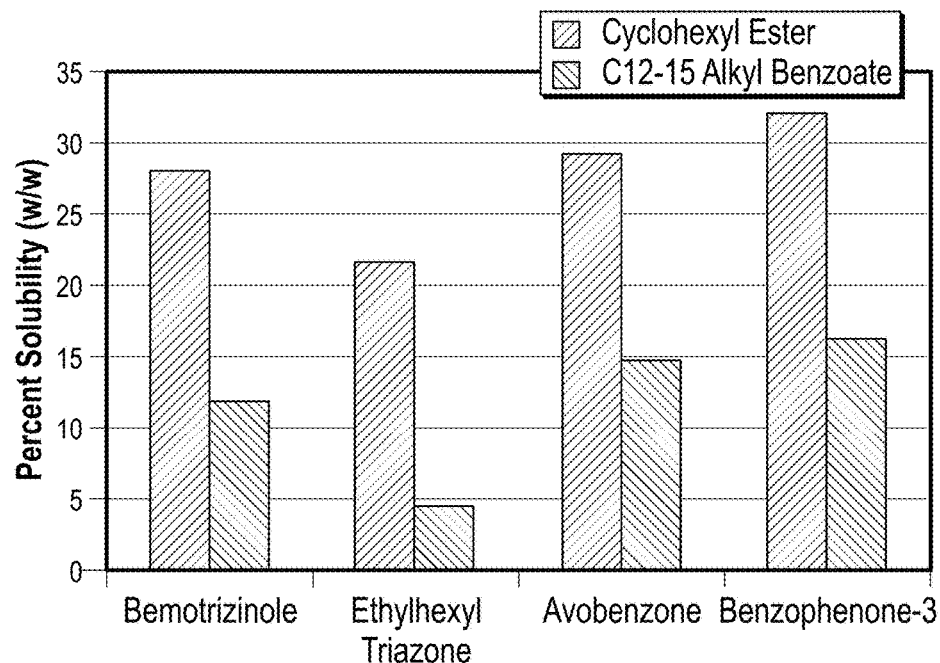
FIG. 3 illustrates solubility of sunscreen agents in cyclohexyl toluate and C12-15 alkyl benzoate at 25° C.
Figure 4:
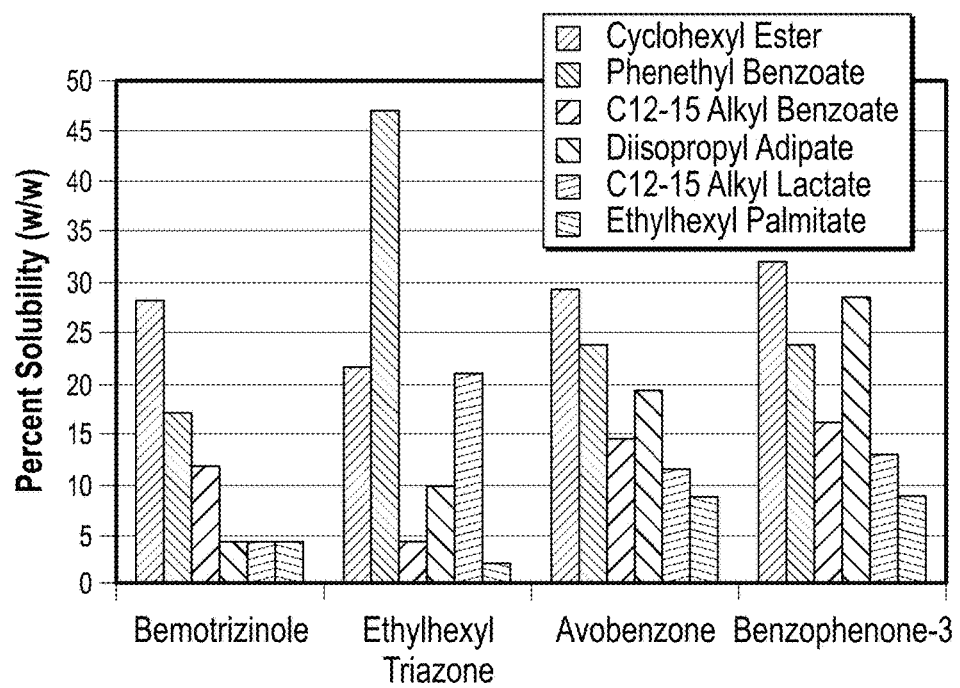
FIG. 4 illustrates solubility of sunscreen agents in cyclohexyl toluate and various esters.
Figure 5:
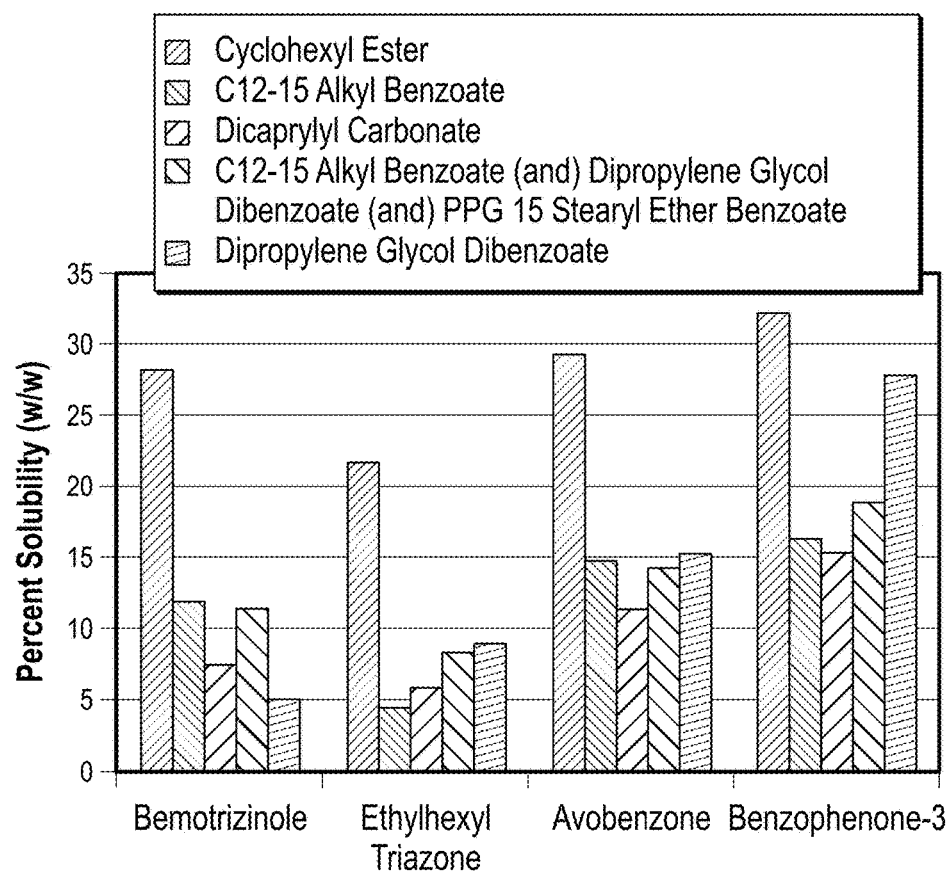
FIG. 5 illustrates solubility of sunscreen agents in cyclohexyl toluate and various esters.
Figure 6:
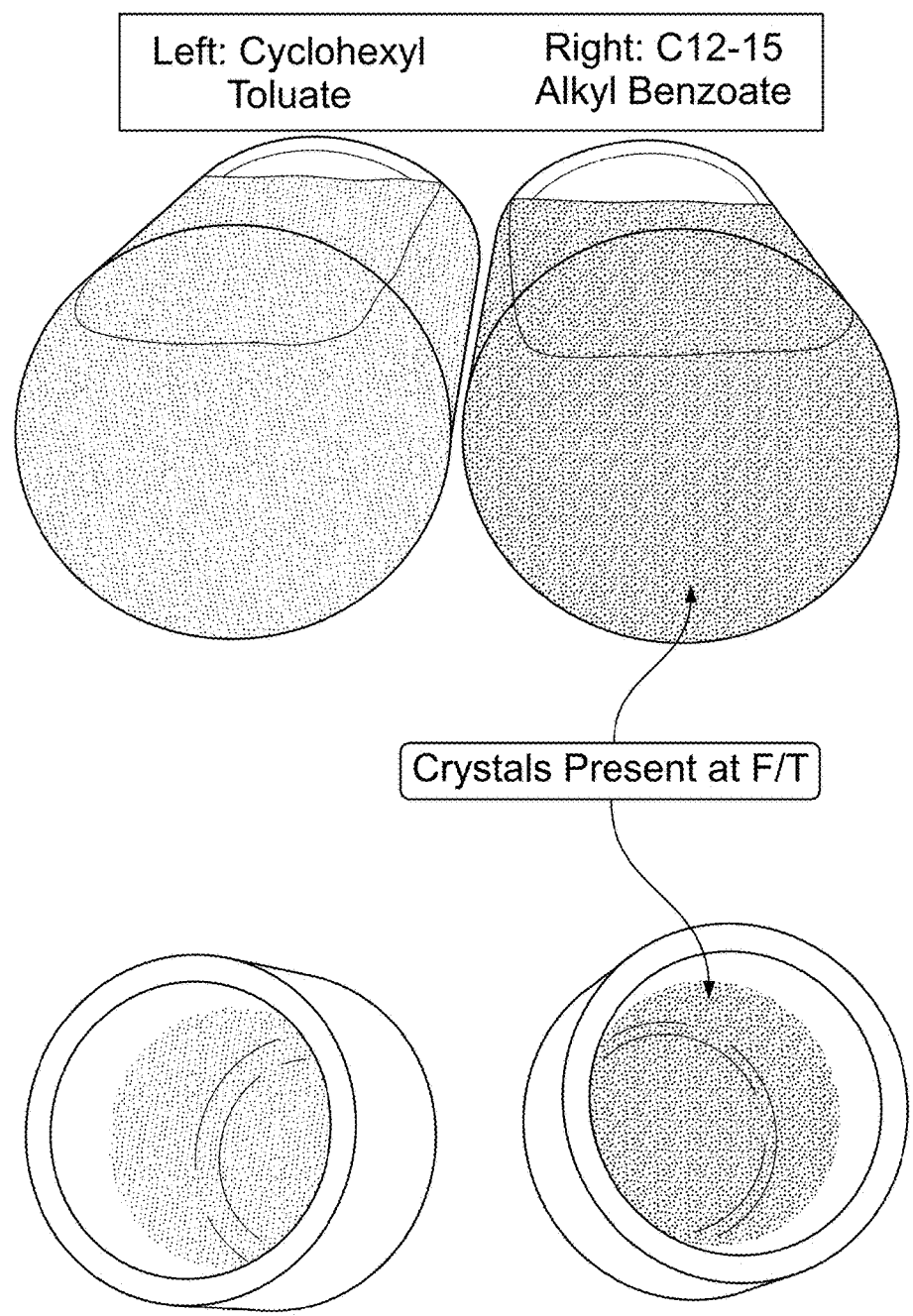
FIG. 6 illustrates solubility comparison in Cyclohexyl Toluate and C12-15 Alkyl Benzoate.

Example 8: Comparison Studies of Sunscreens with Cycloalkyl Toluate and Other Solubilizing Compounds Different samples of the current solubilizing compound cycloalkyl toluate was combined with available sunscreens Escalol S, avobenzone and oxybenzone at 25° C. The tests show clear solution whereas samples with commercial sunscreen solubilizers X-Tend® 226 and Finsolv® TN show crystal formations. The results are shown in FIG. 6. Solubility was checked for cyclohexyl ester in various sunscreen actives such as bemotrizinol, ethylhexyl triazone, avobenzone & benzophenone-3 in comparison to phenethyl benzoate. It was observed that cyclohexyl ester was best solubilizer for Bemotrizinole, avobenzone and benzophenone-3 over phenethyl benzoate, the results are provided in FIG. 2. Sunscreen active comprising cyclohexyl toluate as solubilizer shows increased solubility percentages of about 22% to about 33%, compared to sunscreen active comprising C12-15 alkyl benzoates as solubilizers which showed around 4% to around 15% of solubility, the results are depicted in FIG. 3. Similar results are observed when sunscreen actives are screened for other esters as solubilizers selected from phenethyl benzoate, diisopropyl adipate, C12-15 lactate, ethylhexyl palmitate, dicaprylyl carbonate, C12-15 alkyl benzoate (and) dipropylene glycol dibenzoate (and) PPG 15 stearyl ether benzoate, dipropylene glycol dibenzoate and compared with sunscreen comprising cyclohexyl toluate, results are shown in FIG. 4 & FIG. 5.

Example 9: Expert Odor Evaluations

| Product | Chasis | Cyclohexyl Toluate % w/w | Bemotrizinol level % w/w | Fresh Sample | Aged Sample |
|---|---|---|---|---|---|
| SPF 30 Cream | O/W cream | 5.00 | 1.00 | Accepted | Accepted |
| SPF 20 Cream | O/W cream | 5.00 | 3.00 | Accepted | Accepted |
| Spray | Anhydrous | 3.00 | 2.00 | Accepted | Accepted |

Sunscreen having cyclohexyl toluate and bemotrizinol as solubilizers were tested for odor by an expert panel of 12 members and appreciable level of odor acceptance results were reported. Odor acceptance and odor preference values are shown in FIG. 1.

Example 10—Formulation—Comparison of Solubility

| Ingredient Name | Sample A % w/w | Sample B % w/w |
|---|---|---|
| Phase A | | |
| Alcohol Denatured | 51.00 | 51.00 |
| Phase B | | |
| Butyl Methoxy dibenzoyl methane (Avobenzone) | 3.00 | 3.00 |
| Octisalate | 5.00 | 5.00 |
| Bis-ethylhexyloxyphenol methoxy phenyl triazine (Bemotrizinol) | 3.00 | 3.00 |
| Homosalate | 10.00 | 10.00 |
| Ethylhexyl triazone | 3.00 | 3.00 |
| Isodecyl neopentanoate | 10.00 | 10.00 |
| Diisopropyl adipate | 5.00 | 5.00 |
| C12-15 Alkyl Benzoate | — | 10.00 |
| Cyclohexyl toluate | 10.00 | — |
| Total | 100.00 | 100.00 |

Sample A had cyclohexyl toluate as solubilizer and Sample B had C12-15 alkyl benzoate. When two samples were tested for solubility, it showed that no crystals were formed in Sample A whereas Sample B showed crystals. The results are depicted in FIG. 1.

Example 11—Formulation—Anhydrous Spray

| Ingredient Name | Sample C % w/w |
|---|---|
| Phase A | |
| Alcohol Denatured | 40.25 |
| Vinyl Acetate/Butyl Maleate/Isobornyl Acrylate copolymer | 2.00 |
| Phase B | |
| Butyl Methoxydibenzoylmethane | 3.00 |
| Bis-ethylhexyloxyphenol methoxy phenyl triazine (Bemotrizinol) | 2.00 |
| Octisalate | 5.00 |
| Homosalate | 10.00 |
| Octocrylene | 8.00 |
| Isocetyl alcohol | 5.00 |
| Dicaprylyl carbonate | 5.25 |
| 2-ethylhexyl isononanoate | 5.50 |
| Phase C | |
| Caprylyl methicone | 7.00 |
| Cyclopentasiloxane | 2.00 |
| Cyclohexyl toluate | 5.00 |
| Total | 100.00 |

An anhydrous spray was prepared using cyclohexyl toluate (5%). A clear yellow liquid was obtained.

Example 12—Formulation—Anhydrous Spray

| Ingredient Name | Sample D % w/w |
|---|---|
| Phase A | |
| Alcohol Denatured | 42.25 |
| VA/Butyl Maleate/Isobornyl Acrylate copolymer | 2.00 |
| Phase B | |
| Butyl Methoxydibenzoylmethane | 3.00 |
| Bis-ethylhexyloxyphenol methoxy phenyl triazine (Bemotrizinol) | 3.00 |
| Octisalate | 5.00 |
| Homosalate | 10.00 |
| Octocrylene | 5.00 |
| Isocetyl alcohol | 5.00 |
| Coco-caprylate Caprate | 5.25 |
| 2-ethylhexyl isononanoate | 5.50 |
| Phase C | |
| Caprylyl methicone | 7.00 |
| Cyclopentasiloxane | 2.00 |
| Cyclohexyl toluate | 5.00 |
| Total | 100.00 |

An anhydrous spray was prepared using cyclohexyl toluate (5%). A clear yellow liquid was obtained.

Example 13—Formulation—Anhydrous Spray

| Ingredient Name | Sample E % w/w |
|---|---|
| Phase A | |
| Ethanol | 44.00 |
| VA/Butyl Maleate/Isobornyl Acrylate copolymer | 2.00 |

| Ingredient Name | Sample E % w/w |
|---|---|
| Phase B | |
| Butyl Methoxydibenzoylmethane (Avobenzone) | 3.00 |
| Octisalate | 5.00 |
| Homosalate | 10.00 |
| Octocrylene | 8.00 |
| Bis-ethylhexyloxyphenol methoxy phenyl triazine (Bemotrizinol) | 2.00 |
| Cyclohexyl Toluate | 3.00 |
| Diisopropyl Adipate | 5.00 |
| Lauryl Lactate | 5.00 |
| C12-15 Alkyl lactate | 5.00 |
| Dicaprylyl carbonate | 4.00 |
| Isodecyl Salicylate | 3.00 |
| Total | 100.00 |

An anhydrous spray was prepared using cyclohexyl toluate (3%). A clear yellow liquid was obtained.

Example 14—Formulation—Anhydrous Dry Gel

| Ingredient Name | Sample F % w/w |
|---|---|
| Phase A | |
| Butyl Methoxy dibenzoylmethane | 3.00 |
| Bis-Ethylhexyloxyphenol methoxy phenyl triazine | 2.00 |
| Ethylhexyl Salicylate | 5.00 |
| Homosalate | 10.00 |
| Octocrylene | 8.00 |
| Cyclohexyl Toluate | 5.00 |
| Phase B | |
| Diisopropyl Adipate | 7.00 |
| Isocetyl Alcohol | 2.50 |
| Lauryl Lactate | 6.50 |
| Isodecyl Neopentanoate | 1.00 |
| Ethylhexyl Isononanoate | 2.00 |
| Phase C | |
| Acrylates/C12-22 Alkyl Methacrylate Copolymer (and) Water/Aqua (and) Propylene glycol | 1.00 |
| PolyVinylPyrrolidone | 4.00 |
| Alcohol Denatured | 43.00 |
| Total | 100.00 |

An anhydrous dry gel was prepared using cyclohexyl toluate (5%). Viscosity (D1): 30000-35000 cps as measured by (Brookfield RVT/T C/5 rpm/25 C/1 min)

Example 15—Formulation—Gel Cream SPF 20

| Ingredient Name | Sample G % w/w |
|---|---|
| Phase A | |
| Water | 61.78 |
| Glycerin | 2.00 |
| Propylene Glycol | 3.00 |
| Triethanolamine | 0.05 |
| Acrylic acid/Vinyl Pyrrolidone crosspolymer | 0.30 |
| Phenoxyethanol (and) Methyl paraben (and) Ethyl paraben (and) Propylparaben | 1.00 |
| Phase B | |
| Homosalate | 10.00 |
| Octocrylene | 5.00 |
| Butyl methoxydibenzoyl methane | 3.00 |
| Bis-Ethylhexyloxyphenol Methoxyphenyl triazine | 3.00 |
| Glyceryl Stearate (and) Laureth-23 | 1.00 |
| Ceteareth-20 | 0.50 |
| Cyclohexyl Toluate | 5.00 |
| Phase C | |
| Triethanolamine | 0.70 |
| Phase D | |
| Sodium Polyacrylate (and) Hydrogenated Polydecene (and) Trideceth-6 | 0.30 |
| Phase E | |
| Ethylhexyl isononanoate (and) Cetyl Dimethicone | 1.00 |
| Dimethicone/Vinyl Dimethicone Crosspolymer (and) Isododecane | 3.00 |
| Total | 100.00 |

A gel cream was prepared using cyclohexyl toluate (5%). Viscosity (D1): 27,000-33,000 cps as measured by (Brookfield RVT/TB/5 rpm/25 C/1 min) and pH at 5.75-6.25

Example 16—Formulation—SPF 20 Cream

| Ingredient Name | Sample H % w/w |
|---|---|
| Phase A | |
| Water | 62.50 |
| Glycerin | 3.00 |
| Disodium Ethylene Diamine Tetra Acetic acid (EDTA) | 0.10 |
| Triethanolamine | 0.50 |
| Acrylic acid/VP Crosspolymer | 0.70 |
| Phase B | |
| Dimethicone | 0.50 |
| PEG-20 Methyl Glucose Sesquistearate | 2.50 |
| Methyl Glucose Sesquistearate | 0.50 |
| Cetyl Alcohol | 1.50 |
| Isodecyl neopentanoate | 3.00 |
| Butyl methoxydibezoylmethane (Avobenzoen) | 1.00 |
| Octisalate | 5.00 |
| Octocrylene | 2.00 |
| Bis-Ethylhexyloxyphenol Methoxyphenyl Triazine (Bemotrizinol) | 3.00 |
| Cyclohexyl Toluate | 5.00 |
| Phase C | |
| Cyclopentasiloxane | 5.00 |
| Cyclopentasiloxane (and) Dimethicone/Vinyltrimethylsiloxysilicate Crosspolymer | 1.00 |

-continued

| Ingredient Name | Sample H<br>% w/w |
|---|---|
| Phase D | |
| Phenoxyethanol (and) benzoic Acid (and) Dehydroacetic Acid | 0.75 |
| Total | 100.00 |

SPF 20 cream was prepared using cyclohexyl toluate (5%). Viscosity: 9000-1000 cps was observed as measured by (Brookfield RVT/TB/10 rpm/25 C/1 min) at pH: 5.30-5.70

Example 17—Formulation—SPF 30 Cream

| Ingredient Name | Sample I<br>% w/w |
|---|---|
| Phase A | |
| Water | 62.15 |
| Carbomer | 0.40 |
| Phase B | |
| Avobenzone | 1.00 |
| Octisalate | 5.00 |
| Homosalate | 10.00 |
| Octocrylene | 0.80 |
| Benzopheneone-3 | 4.00 |
| Bemotrizinol | 1.00 |
| Glyceryl Stearate (and) Laureth-23 | 3.00 |
| Ceteareth-20 | 1.50 |
| Cyclohexyl Toluate | 5.00 |
| Phase C | |
| Water | 5.00 |
| Triethanolamine | 0.40 |
| Phase D | |
| Propylene Glycol (and) Diazolidinyl Urea (and) Methylparaben (and) Propylparaben | 0.75 |
| Total | 100.00 |

SPF 30 cream was prepared using cyclohexyl toluate (5%). Viscosity: 30000-35000 cps was observed as measured by (Brookfield RVT/TB/10 rpm/25 C/1 min) at pH: 6.00-6.50.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A photo protective topical composition, comprising:
    i. at least one functional active; and
    ii. at least one solubilizing compound having the formula I,

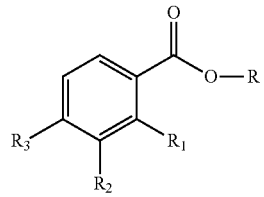

Formula 1 wherein R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H; wherein said compound is present in an amount effective to solubilize said functional active.

2. The composition according to claim 1, wherein said composition is visibly transparent and free of odor.

3. The composition according to claim 1, wherein said solubilizing compound is selected from the group consisting of cyclohexyl 2-toluate, cyclohexyl 3-toluate, cyclohexyl 4-toluate, cyclohexylmethanol 3-toluate, cyclopentyl 3-toluate, cycloheptyl-m-toluate and combinations thereof.

4. The composition according to claim 3, wherein said solubilizing compound is selected from cyclohexyl 3-toluate, cyclohexyl 4-toluate and combinations thereof.

5. The composition according to claim 1, wherein said solubilizing compound is present in an amount of about 0.1% wt./wt. to about 70% wt./wt. of the total photo protective topical composition.

6. The composition according to claim 1, wherein said functional active is present in an amount of about 1% wt./wt. to about 70% wt./wt. of the total photo protective topical composition.

7. The composition according to claim 1, wherein said photo protective topical composition is a personal care, cosmetic care, pharmaceutical or nutraceutical composition.

8. The composition according to claim 1, wherein said functional active is a personal care active, cosmetic care active, pharmaceutical active or nutraceutical active.

9. The composition according to claim 8, wherein said personal care active is a sunscreen active containing Ultra Violet (UV) A and/or UVB active agent.

10. The composition according to claim 8, wherein said personal care composition capable of demonstrating increased retention of UV absorption after exposure to UV radiation.

11. The composition according to claim 9, wherein said sunscreen active is selected from the group consisting of octyl salicylate; p-aminobenzoic acid, PEG-25PABA, Ethylhexyl dimethyl PABA, pentyl dimethyl PABA, octyl dimethyl PABA, amyl dimethyl PABA, benzophenone-1, benzophenone-2, benzophenone-3, benzophenone-4, benzophenone-5, benzophenone-6, benzophenone-8, benzophenone-9, 2-(2H-benzotriazole-2-yl)-4,6-di-tert-pentylphenol, ethyl-2-cyano-3,3-diphenyl acrylate, homo menthyl salicylate, his-ethyl hexyloxyphenol methoxy phenyl triazine (bemotrizinol), methyl-(1,2,2,6,6-pentamethyl-4-piperidyl)-sebacate, 2-(2H-benzotriazole-2-yl)-4-methylphenol, diethylhexyl butamido triazone, 4,6-bis-(octylthiomethyl)-o-cresol, Poly(4-hydroxy-2,2,6,6-tetramethyl-1-piperidine ethanol-alt-1,4-butanedioic acid), red petroleum, octocrylene, isoamyl-p-methoxycinnamate, drometrizole, drometrizole trisiloxane, bisoctrizole, 2,4-di-tert-butyl-6-(5-chloro-2H-benzotriazole-2-yl)-phenol, 2-hydroxy-4-octyloxy benzophenone, diisopropyl methylcinnamate, 2-(1,1-dimethylethyl)-6-[[3-(1,1-demethylethyl)-2-hydroxy-5-methylphenyl]methyl-4-methylphenyl-acrylate, menthyl anthranilate, butyl methoxy dibenzoyl methane, 2-ethoxyethyl p-methoxycinnamate, benzylidene camphor sulfonic acid, dimethoxyphenyl-[1-(3,4)]-4,4-dimethyl1,3-pentanedione, N,N'-hexane-1,6-diylbis-[3-(3,5-di-tert-butyl-4-hydroxyphenyl-propionamide)], pentaerythritol tetrakis [3-(3,5-di-tert-butyl-4-hydroxyphenyl) propionate], 2,6-di-tert-butyl-4-[4,6-bis(octylthio)-1,3,5-triazin-2-ylamino] phenol, 2-(2H-benzotriazole-2-yl)-4,6-bis(1-methyl-1-phenylethyl) phenol, trolamine salicylate, diethylanolamine p-methoxycinnamate, polysilicone-15, 4-methylbenzylidene camphor, n-phenyl-benzenamine, reaction products of 2,4,4-trimethylpentene, (2-ethylhexyl)-2-cyano-3,3-diphenylacrylate, digalloyl trioleate, polyacrylamido methylbenzylidene camphor, glyceryl ethylhexanoate dimethoxycinnamate, 1,3-bis-[(2'-cyano-3',3'-diphenylacryloyl)oxy]-2,2-bis-{[(2'-cyano-bis-(2,2,6,6-tetramethyl-4-piperidyl)-sebacate, 1,3,5-tris(3, 5-di-tert-butyl-4-hydroxybenzyl)-1,3,5-triazine-2,4,6(1H, 3H, 5H)-trione, hexamethylendiamine, ethyl-4-bis(hydroxypropyl) aminobenzoate, 6-tert-butyl-2-(5-chloro-2H-benzotriazole-2-yl)-4-methyl phenol, 3,3',3",5,5',5"-hexa-tert-butyl-α-α'-α"-(mesitylene-2,4,6-triyl) tri-p-cresol, ethylhexyl dimethoxybenzylidene dioxoimidazoline propionate, N,N'-bisformyl-N,N'-bis-(2,2,6,6-tetramethyl-4-piperidinyl), 3-benzylidene camphor, terephthalylidene dicamphor sulfonic acid, camphor benzalkonium methosulfate, bisdisulizole disodium, etocrylene, ferulic acid, 2-(2H-benzotriazole-2-yl)-4-(1,1,3,3-tetramethylbutyl)-phenol, 4,6-bis(dodecylthiomethyl)-o-cresol, β-2-glucopyranoxy propyl hydroxy benzophenone, phenylbenzimidazole sulfonic acid, diethylamine hydroxy benzoyl hexylbenzoate, 3',3'-diphenylacryloyl)oxy]methyl}-propane, ethylhexyl p-methoxycinnamate, avobenzone, camphor benzalkonium methosulfate, phenylbenzimidazole sulfonic acid, terephthalidene dicamphor sulfonic acid, benzylidene camphor sulfonic acid, polyacrylamidomethyl benzylidene camphor, ethylhexyl methoxycinnamate, ethylhexyl triazone, diethylhexyl butamido triazone, 4-methylbenzylidene camphor, 3-benzylidene camphor, methylene-bis-benztriazolyl tetramethylbutylphenol, disodium phenyl dibenzimidazole tetrasulfonate, bisethylhexyloxyphenol methoxyphenol triazine, polysilicone-15, 2,4,6-tris(Diisobutyl 4-aminobenzalmalonate)-s-triazine, titanium dioxide, zinc oxide, micronized or unmicronized mixtures thereof.

12. The composition according to claim 9, wherein said sunscreen active is present in an amount of about 1% wt./wt. to about 70% wt./wt. of the total composition.

13. The composition according to claim 11, wherein said sunscreen active is bisethylhexyloxy phenol methoxyphenol triazine.

14. The composition according to claim 1, wherein said composition further comprises a mineral photo protective agent present in an amount of about 0.01% wt./wt. to about 70% wt./wt. of the total composition.

15. The composition according to claim 14, wherein said photo protective agent is treated or untreated metal oxide pigments or nanopigments selected from the group consisting of treated or untreated titanium oxide, zinc oxide, iron oxide, zirconium oxide, cerium oxide and mixtures thereof.

16. The composition according to claim 1, wherein said composition further comprises at least one agent for artificially tanning and/or browning the skin selected from dihydroxy acetone, isatin, alloxan, ninhydrin, glyceraldehyde, mesotartaric aldehyde, glutaraldehyde, erythrulose alone or in combination thereof.

17. The composition according to claim 1, wherein said composition further comprises at least one adjuvant or additive selected from secondary polymers for improving water-resistance, UV active solubilizers, oils, waxes, solvents, emulsifiers, preservatives, antioxidants, vitamins, insect repellants, dyes, pigments, humectants, fillers, thickeners, film formers, stabilizers, buffers, spreading agents, pearlizing agents, electrolytes, acids, bases, fatty substances, ionic thickeners, non-ionic thickeners, hydrophilic thickeners, lipophilic thickeners, softeners, opacifiers, emollients, silicones, antifoaming agents, fragrances, anionic surfactants, cationic surfactants, nonionic surfactants, zwitterionic surfactants, amphoteric surfactants, active agents, propellants, acidifying or basifying agents, antioxidants, α-hydroxy acids, moisturizing agents, anti-inflammatory, colorants, pharmaceutically or dermatologically or cosmetically acceptable excipients, and combinations thereof.

18. The composition according to claim 1, wherein said photo protective topical composition is formulated into an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous formulation, an anhydrous spray, an anhydrous gel, an anhydrous dry gel, an aqueous gel, a gel cream SPF 20, a SPF 30 cream, an alcoholic solution, a hydro-alcoholic solution, a milk, a lotion, a powder, a stick, a roll-on, a mist, a wipe, a wax, a mousse, an aerosol, a balm, a patch, a pomade, a pump spray, a solution, a towelette, a paste, a powder or a spray.

19. A method for cosmetically treating or caring for the skin, lips, nails, hair, ears, eyelashes, eyebrows and/or scalp comprising topically applying an effective amount of a photo protective topical composition comprising (i) at least one functional active; and (ii) at least one solubilizing compound having the formula I:

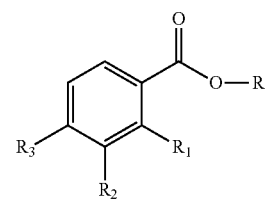

Formula 1 wherein R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H;

wherein said solubilizing compound is present in an amount effective to solubilize said functional active.

20. A method for photo protecting the exposed and/or unexposed skin, nails, hair, lips, ears, eyebrows, eyelashes, and/or scalp, against the damaging effects of UV-irradiation comprising topically applying an effective amount of a cosmetic/dermatological composition comprising: (i) at least one active, and (ii) at least one solubilizing compound having the formula I Formula 1

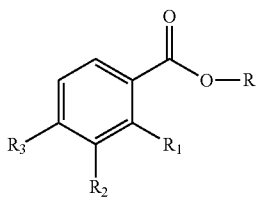

wherein R is $C_5$-$C_{10}$ cycloalkyl or linear or branched alkylcycloalkyl, wherein the ring size is $C_5$-$C_7$; $R_1$, $R_2$, and $R_3$ are each independently selected from the group consisting of H, and linear or branched $C_1$-$C_4$ alkyl, provided that at least two of $R_1$, $R_2$, $R_3$ are H;

wherein said solubilizing compound is present in an amount effective to solubilize said functional active.

21. A photo protective topical sunscreen composition for the UV-photo protection of human skin and/or hair comprising:
a) about 1% wt./wt. to about 70% wt./wt. of at least one active sunscreen agent of claim 11;
b) about 0.1% wt./wt. to about 50% wt./wt. of at least one solubilizing compound selected from cyclohexyl 3-toluate, cyclohexyl 4-toluate or combination thereof; and
c) about 1% wt./wt. to about 80% wt./wt. of at least one topically applicable cosmetically or dermatologically acceptable carrier.

22. The composition according to claim 21, wherein said composition further comprises at least one adjuvant or additive selected from secondary polymers for improving water-resistance, UV active solubilizers, oils, waxes, solvents, emulsifiers, preservatives, vitamins, insect repellants, dyes, pigments, humectants, fillers, film formers, stabilizers, buffers, spreading agents, pearlizing agents, electrolytes, acids, bases, fatty substances, organic solvents, ionic thickeners, non-ionic thickeners, hydrophilic thickeners, lipophilic thickeners, softeners, opacifiers, emollients, silicones, antifoaming agents, fragrances, anionic surfactants, cationic surfactants, nonionic surfactants, zwitterionic surfactants, amphoteric surfactants, active agents, fillers, propellants, acidifying or basifying agents, antioxidants, α-hydroxy acids, moisturizing agents, anti-inflammatory agents, colorants, pharmaceutically or dermatologically or cosmetically acceptable excipients, and combinations thereof.

* * * * *